(12) United States Patent
Tofani

(10) Patent No.: US 8,192,969 B2
(45) Date of Patent: Jun. 5, 2012

(54) APPARATUS AND METHOD FOR INTERFERING WITH PATHOLOGICAL CELLS SURVIVAL PROCESSES

(76) Inventor: Santi Tofani, Burolo (IT)

(*) Notice: Subject to any disclaimer, the term of this patent is extended or adjusted under 35 U.S.C. 154(b) by 354 days.

(21) Appl. No.: 11/168,090

(22) Filed: Jun. 28, 2005

(65) Prior Publication Data

US 2005/0267535 A1 Dec. 1, 2005

Related U.S. Application Data

(63) Continuation of application No. 09/720,549, filed as application No. PCT/EP99/04385 on Jun. 23, 1999, now abandoned.

(30) Foreign Application Priority Data

Jun. 24, 1998 (EP) .................................... 98830381

(51) Int. Cl.
*C12N 13/00* (2006.01)
(52) U.S. Cl. ........................................ 435/173.1; 607/1
(58) Field of Classification Search .......................... None
See application file for complete search history.

(56) References Cited

U.S. PATENT DOCUMENTS 4,665,898 A 5/1987 Costa et al.

OTHER PUBLICATIONS

Zhang et al. Science in China (Series C), 1997, vol. 40, No. 4, p. 392-397.*
Levin et al. Bioelectromagnetics, 1997, vol. 18, p. 255-263.*
Grundler et al., Naturwissenschaften, 1992, vol. 79 p. 551-559.*
Blank M (1993): "Electricity and Magnetism in Biology and Medicine". The First World Congress for Electricity and Magnetism in Biology and Medicine, Orlando, Florida, pp. 1-22.
Liboff AR, Williams T Jr, Strong DM and Wistar R. Jr. (1984): "Time-Varying Magnetic Fields: Effect on DNA Synthesis". Science, vol. 223, pp. 818-820.
Tofani S, Ferrara A, Anglesio L, Gilli G (1995):"Evidence for genotoxic effects of resonant ELF magnetic fields". Bioelectrochemistry and Bioenergetics 36, pp. 9-13.
Phillips jl, Haggren w, Thomas WJ Ishida-Jones T and Adey WR (1992): "Magnetic field-induced changes in specific gene transcription". Biochimica et Biophysica Acta 1132, pp. 140-144.
Liboff AR (1985): Cyclotron resonance in membrane transport. In Chiabrera A, Nicolini C., Schwan HP (eds): "Interactions Between Electromagnetic Fields and Cells". New York: Plenum Press, pp. 281-296.
Lednev VV (1991): "Possible mechanism for the influence of weak magnetic fields on biological systems". Bioelectromagnetics 12, pp. 71-75.
Blanchard JP, Blackman CF (1994):Clarification and application of an ion parametric resonance model for magnetic field interactions with biological systems. Bioelectromagnetics 15, pp. 217-238.
Grundler W, Kaiser F, Keilmann F, Walleczek J (1992): "Mechanisms of electromagnetic interaction with cellular systems". Naturwissenschaften 79, pp. 551-559.
Polk C (1992): "Dosimetry of extremely-low-frequency magnetic fields". Bioelectromagnetics Suppl 1, pp. 209-235.
Walleczek J, Budinger TF (1992): "Pulsed magnetic field effects on calcium signalling in lymphocytes: Dependence on cell status and field intensity". FEBS Lett 314, pp. 351-355.
Steiner UE and Ulrich T (1989): "Magnetic Field Effects in Chemical Kinetics and Related Phenomena". Chem. Rev. 89, pp. 51-147.
Lander HM (1997): "An essential role for free radicals and derived species in signal transduction". The FASEB Journal 11, pp. 118-124.
Polyak K, Xia Y, Zweier JL, Kinzier KW and Volgestein B (1997): "A model for p53-induced apoptosis". Nature vol. 389, pp. 300-305.
Cadossi R, Bersani F, Cossarizza A, Zucchini P, Emilia G, Torelli G and Claudio Franceschi (1992): "Lymphocytes and low-frequency electromagnetic fields". The FASEB Journal vol. 6, pp. 2667-2674.
Walleczeck J (1996): "Electromagnetic Field Effects on Cellular Signal Transduction and Free Radical Mechanisms". Abstract Book XXVth General Assembly of the International Union of Radio Science-Lille-France, p. 547.
Davies RJ, Weidema WF, Sandle GI, Palmer LI, Deschener EE, DeCosse JJ. "Sodium transport in a mouse model of colonic cancer." Cancer Res. 1987: 47:4646-50.
Goller DA, Weidema WF, Davies RJ. "Transmural electrical potential as an early marker in colon cancer." Arch. Surg. 1986: 121:345-50.
Cuzick J, Holland R., Barth V, Davies R, Faupel M, Fentiman I, Frischbier HJ, LaMarque JL, Merson M, Sacchini V, Vanel D, Veronesi U. "Electropotential measurements as a new diagnostic modality for breast cancer." The Lancet 1998: 352:359-363.

(Continued)

*Primary Examiner* — Kade Ariani
(74) *Attorney, Agent, or Firm* — Dennison, Schultz & MacDonald

(57) ABSTRACT

A method and an apparatus for interfering with pathological cells survival processes, i.e. inducing directly or indirectly apoptosis, on living pathological cells, by using magnetic fields without adversely affecting normal cells. Static (S) and extremely low frequency (ELF) magnetic fields are used having low intensity comprised between 1 and 100 mT, preferably comprised between 1 and 30 mT. In particular SELF fields are used which are different sequences of S and/or ELF fields, i.e. S fields followed by ELF fields, ELF fields followed by S fields, S and ELF field together, as well as the presence of S or ELF fields alone, said ELF fields having a field frequency comprised between 1 and 1000 Hz. An apparatus for carrying out the method comprises means for generating static magnetic (S) fields crossing a working environment and/or means for generating electromagnetic extremely low frequency (ELF) fields over the working environment in addition to the S fields. Means are provided for modulating the S fields associated to the S fields generating means and varying the intensity of the S fields from 1 to 100 mT, preferably between 1 to 30 mT according to a predetermined function. Means may also be provided for modulating the ELF fields associated to the ELF fields generating means and imposing to the ELF fields a frequency between 1 and 1000 Hz with intensity comprised between 1 to 100 mT, preferably between 1 and 30 mT according to a predetermined function.

8 Claims, 5 Drawing Sheets

OTHER PUBLICATIONS

Narita K, Hanakawa K, Kasahara T, Hisamitsu T, Asano K (1997): "Induction of apoptotic cell death in human leukemic cell line, HL-60, by extremely low frequency electric magnetic fields: analysis of the possible mechanisms in vitro". In vivo 111(4), pp. 329-335.

Raylman RR, Clavo AC, Wahl RL (1996): "Exposure to Strong Static Magnetic Field Slow the Growth of Human Cancer Cells In Vitro". Bioelectromagnetics 17, pp. 358-363.

Haberkorn R, Michel-Beyerle ME. "On the mechanism of magnetic field effects in bacterial photosynthesis." Biophysical Journal 1979: 26:489-498.

Lersch W, Michel-Beyerle ME. "Magnetic field effects on the recombination of radical ions in reaction centers of photosynthetic bacteria." Chemical Physics 1983: 78:115-126.

Scaiano JC, Mohtat N, Cozens FL, McLean J and Thansandote (1994): "Application of the Radical Pair Mechanism to Free Radicals I Organized Systems: Can the Effects of 60 Hz Be Predicted From Studies Under Static Fields?" Bioelectromagnetics 15, pp. 549-554.

Engstrom S (1997): "What is the Time of Magnetic Field Interaction in Biological Systems?". Bioelectromagnetics 18, pp. 244-249.

B.S. Thornton (1984): "Inversion of raman spectra of living cells indicates dielectric structure related to energy control", in Physics Letters, vol. 106A, pp. 198-202.

S.T. Barsamian (1987): "Dielectric origin of living cells", in Biophysical Aspects of Cancer, Charles University Prague, pp. 152-159.

Phillips, Jerry L; Haggren, Wendy; Thomas, william J.; Ishida-Jones, Tamako. "Magnetic field-inducted changes in specific gene transcription." Biochimica et Blophysica Acta. 1132, 1992, pp. 140-144.

Adey, W. Ross. "Electromagnetics in Biology and Medicine." Modern Radio Science 1993, pp. 231-249.

* cited by examiner

APPARATUS AND METHOD FOR INTERFERING WITH PATHOLOGICAL CELLS SURVIVAL PROCESSES

RELATED APPLICATION

This application is a continuation of U.S. patent application Ser. No. 09/720,549, filed Dec. 22, 2000 now abandoned, which application is hereby incorporated by reference. This application claims the benefit of European Patent Application EP98830381.4 filed Jun. 24, 1998 and PCT/EP99/04385 filed Jun. 23, 1999.

FIELD OF THE INVENTION

The present invention generally relates to an apparatus for interfering with pathological cells survival processes.

In addition, the invention relates to a microbiological method carried out by such apparatus for interfering with pathological cells' survival, in particular cells affected by cancer and other diseases caused by alterations in the mechanism of cell survival.

In particular, the interference is induced by means of static (S) and extremely low frequency electromagnetic (ELF) fields produced by the apparatus.

Magnetic Static fields and Extremely Low Frequency electromagnetic fields are hereinafter referred to as S and ELF, respectively. Moreover, any possible combination of different sequences of S and/or ELF fields, such as S fields followed by ELF fields, ELF fields followed by S fields, S and ELF field together, as well as the presence of S or ELF fields alone, will hereinafter be referred to also as SELF fields.

BACKGROUND OF THE INVENTION

It is known that pericellular fields and currents induced by an Extremely Low Frequency (ELF) electromagnetic field, whose frequency range is from 1 Hz to 300 Hz and perhaps up to 1000 Hz, induce within the cell certain membrane electrochemical events which are important for primary biologic signal transduction and amplification processes.

These biochemically mediated events then produce cytoplasmic second messengers and internal effectors such as free $Ca^{++}$ and protein phosphorylases (kinases) which in turn trigger certain changes in the biosynthesis of macromolecules as well as bring about alterations in cellular growth differentiation and functional properties [[1]M. Blank, 1993].

Further, the possibility that S and ELF fields affect the DNA synthesis, DNA integrity, transcription and translation has been documented [[2]Liboff 1984, [3]Tofani 1995, [4]Goodman 1991, [5]Phillips 1992].

A possible physical mechanism to account for some of the experimental findings is the direct effect on ions (i.e., $Ca^{++}$) or on ligand binding at the cell membrane [[6]Liboff 1985, [7]Chiabrera 1985, [8]Lednev 1991, [9]Blanchard 1994].

The possibility of influencing variations of $Ca^{++}$ metabolism may lead to cell apoptosis (programmed cell death) [[10]Preston, [11]Trump 1997].

Another physical interaction mechanism is related to the possibility of influencing the kinetics of appropriate cell signalling pathways of the cell (including calcium metabolism) through a field direct effect on electron-spin motion of atoms and molecules with unpaired electrons. This influencing may affect the recombination ratio of a spin correlated free radical pair and consequently on redox signalling [[12]Grundler 1992; [13]Polk 1992; [14]Walleczek and Budingher 1992; [15]Adey 1993].

In particular, the spin singlet-triplet energetic level transition in a free radical is critical for increasing the recombination ratio of spin correlated free radical pairs.

The possibility for low level, non thermal (with intensity up to 30 mT) S and ELF magnetic fields to influence in vitro the kinetics and efficacy of radical pair reactions is known from magnetochemistry [[16]Steiner 1989].

Naturally occurring free radicals have an oxygen- or nitrogen-based unpaired electron such as superoxide anion, hydroxyl radical and nitric oxide. These Reactive Oxygen Species (ROS) and Reactive Nitrogen Species (RNS) can target proteins providing an obvious mechanistic explanation for free radicals-mediated signalling events. These events may influence growth factors, ion transport (i.e. $Ca^{++}$ channels), transcription, apoptosis [[17]Lander 1997].

Apoptosis is a morphologically distinct form of programmed cell death that is connected in cell survival processes playing an important role during development, homeostasis, and in many diseases including cancer, acquired immunodeficiency syndrome, and neurodegenerative disorders, as well as in other diseases that similarly to those are characterised by altered cell survival processes. Apoptosis occurs through the activation of a cell-intrinsic suicide program. The basic genetic mechanism of apoptosis appears to be present in essentially all mammalian cells at all times, but the activation of this suicide program is regulated by many different signals that originate from both the intracellular and the extracellular environment.

Among all the genes involved in apoptosis regulation, the p53 gene is receiving much attention. This gene, which encodes a transcription factor and is common in many human cancers, mediates the cellular responses to some environmental damage. The p53 protein either can temporarily stop cell division, so that the cell can repair altered DNA, or can pilot the cell to an apoptotic death.

Published data support that p53 appears in apoptosis through a three step process: 1) transcriptional induction of redox-related genes: 2) the formation of reactive oxygen species and 3) the oxidative degradation of mitochondria components, culminating in cell death [[18]Polyak 1997].

In addition anti-oxidative agents are combined with drugs in the treatment of hypoxia tumour cells [19] [Walch, 1988] and in the influence of vascular growth factor [20][Amirkhosravi, 1998].

Moreover, published data are supporting the idea that pathological cells answer differently than normal cells to ELF fields stimuli. According to [21]Cadossi [1992], lymphocytes from normal patients respond differently than lymphocytes from Down's syndrome, AIDS and chronic lymphocytic leukaemia patients when exposed to ELF fields (previously with mitogen).

It is also recognised that $Ca^{++}$ influx across the membrane is influenced by ELF fields in leukaemic lymphocytes but not in normal lymphocytes [[22]Walleczek, 1996].

Altered cell survival processes come with electric disorders and different electrical behavior. In fact, rapidly proliferating and transformed cells have electrically depolarized cell membranes if compared with normal cells [[23]Binggeli, 1986; [24]Marino 1994]. It has also been shown that epithelial cells lose their transepithelial potential during carcinogenesis [[25]Davies 1987; [26] Goller 1986; [27]Capko, 1996]. This different electrical behavior of tumor cells compared with normal cells is the basis for a newly proposed cancer diagnostic modality [[28]Cuzick 1998]. In addition, the concentration of free radicals in transformed cells and tissues is higher than in non-transformed ones [[29]Szatrowski 1991; [30]Shulyakovskaya 1993; [31]Iwagaki 1995].

With reference to chemotherapy all efforts are devoted to the target of inducing cell apoptosis in vivo instead of killing them, through Signal Transduction Directed Therapy (STDT) of cancer [32Levin, 1998].

Signal Transduction is a functional term that connotes the translation of genetic information into signalling cascades that allow the cell to for example interpret and respond to external stimuli and/or duplicate itself Recent evidence suggests that alterations in the cell survival processes contribute to the pathogenesis of a number of human diseases, including cancer, viral infections, autoimmune diseases, neurodegenerative disorders, and AIDS. Treatments designed to specifically alter the apoptotic threshold connected with the survival processes mechanisms may have the potentiality to change the natural progression of some of these diseases [33Thompson, 1995].

High intensity electrical, electromagnetic and magnetic fields have been used to destroy pathological cells.

In [34]U.S. Pat. No. 4,665,898 an apparatus is described in which animals having malignant cells are treated by means of a high intensity pulsed magnetic field, in order to neutralise/destroy malignant cells in a selective way. This apparatus produces magnetic thermal fields having intensity comprised between 1 Tesla up to 10 Tesla and reversing polarity in the range 5÷1000 Kilohertz. In the preferred embodiment the magnetic field intensity is set between 1 and 50 Tesla and in particular, in the examples, it is set at 5 Tesla and 8 Kilohertz up to 18 Tesla and 250 Kilohertz.

Different ELF, thermal, continuous or pulsed fields have been used for anti-cancer therapy in vitro [35Narita, 1997; 36Raylman, 1996].

In these cases the fields are of very high intensity, much higher than what people are allowed to be exposed by the safety standards, and may produce heating thus damaging normal tissues and cells.

ELF low intensity electromagnetic fields have been used as well to inhibit mitosis of malignant cells, such as in DE 4122380A1 and U.S. Pat. No. 5,156,587. However, these documents describe the use of sinusoidal fields only at a fixed net frequency and at a fixed intensity, with the possibility to sweep only a limited range of energy levels inside the cellular tissue.

SUMMARY OF THE INVENTION

It is an object of the present invention to provide a method for interfering with cell survival processes (i.e. inducing apoptosis) of living pathological cells (i.e. cancer cells) by using magnetic fields without adversely affecting normal cells.

It is another object of the invention to provide an apparatus for interfering with pathological cells survival processes.

The former and other objects are reached by the method for interfering with pathological cells survival according to the invention whose characteristic is to apply to living pathological cells (i.e. cancer cells and cells affected by other diseases caused by alterations in the mechanism of cell survival) non thermal SELF magnetic fields to induce apoptosis in a selective way.

For the purposes of the invention SELF fields are to be considered as different sequences of S and/or ELF fields, i.e. S fields followed by ELF fields, ELF fields followed by S fields, S and ELF field together, as well as the presence of S or ELF fields alone.

The concept underlying the method according to the invention is that SELF fields interfere with cell signalling sustaining cell pathological behaviour inside pathological cells, i.e. on redox signalling through free radicals, thus restoring the cell survival processes, i.e. inducing directly or indirectly apoptosis through a modification of p53 gene expression.

This method is supposed to recombine oxygen-based free radicals and may also be used as an anti-oxidative agent. Its combination with drugs in the treatment of hypoxia tumour cells and in the influence of vascular growth factor may also be considered.

The reason why SELF fields selectively induce apoptosis in pathological cells (i.e. cancer cells) may be related to the altered electrical behaviour of pathological cells compared with that of normal cells.

For these reasons SELF fields can induce directly or indirectly a signal programmed cell death (apoptosis), in vitro and in vivo, without causing any adverse effect.

In the hypothesis that free radicals recombination is at the basis of the expected biological effects on pathological cells (i.e., anti-tumour activity) the transition between singlet-triplet of unpaired electron in oxygen based free radicals has to be considered. In fact this transition, which depends on the applied magnetic field, is critical for increasing the recombination ratio of a spin correlated free radical pair. However, the reaction centers related to the expected anti tumor effect are unknown and therefore the lifetime of the spin states and the energy splitting between singlet and triplet states cannot be precisely determined from the spin hamiltonian [37Haberkorn 1979, 38Lersch 1983].

To encompass this problem, according to the invention, sequences of S magnetic fields with different intensity modulated in amplitude can be used, with the superimposition of ELF magnetic fields. The use of modulated fields is in agreement with the need for reaching optimal condition(s) for the singlet-triplet spin state conversion required for the free radical recombination processes [13Polk 1992].

For these reasons, S, ELF or SELF fields have higher probability to induce the expected biological effects if they are modulated following a predetermined function of intensity and or frequency versus time, since this way the probability to induce the above transition is higher.

The different sequences of S and/or ELF fields sequences are advantageously set for time intervals $T_1$, $T_2$, $T_3$, $T_n$, wherein the intensity $I_S$, $I_{ELF}$ and their ratio $I_S/I_{ELF}$ are set at steady values $I_{S1}$, $I_{S2}$, $I_{S3}$, $I_{Sn}$; $I_{ELF1}$, $I_{ELF2}$, $I_{ELF3}$, $I_{ELFn}$, $I_{S1}/I_{ELF1}$, $I_{S2}/I_{ELF2}$, $I_{S3}/I_{ELF3}$, $I_{Sn}/I_{ELFn}$, respectively.

For the same reasons modulated SELF non thermal fields can be potentially used for treatment of cells affected by many diseases like viral infections, AIDS, autoimmune diseases, etc., where the alteration of cell survival contributes to their pathogenesis.

According to another aspect of the invention, an apparatus for selectively interfering with pathological cells survival processes in vitro and in vivo has the characteristic of comprising means for generating static magnetic (S) fields crossing a working environment and means for generating electromagnetic extremely low frequency (ELF) fields in the working environment alone or in addition to the S fields.

Means are provided for modulating the S fields associated to the means for generating S fields and varying the intensity of the S fields between 1 and 100 mT and preferably from 1 to 30 mT.

Means are also provided for modulating the ELF fields alone or associated to the S fields at a frequency between 1 and 1000 Hz with intensity comprised between 1 and 30 mT. Preferably the ELF fields have a frequency between 10 and 100 Hz.

In a particular embodiment of the invention the means for modulating the S fields comprises program means that alternatively or in combination:

set the intensity following a plurality of predetermined step values $I_{S1}$, $I_{S2}$, $I_{S3}$, $I_{Sn}$ for corresponding time intervals $T_1$, $T_2$, $T_3$, $T_n$;

set the intensity amplitude following a plurality of predetermined step values $I_{ELF1}$, $I_{ELF2}$, $I_{ELF3}$, $I_{ELFn}$ for corresponding time intervals $T_1$, $T_2$, $T_3$, $T_n$;

set the frequency following a plurality of predetermined step values $f_1$, $f_2$, $f_3$, $f_n$, for corresponding time intervals $T_1$, $T_2$, $T_3$, $T_n$;

set an S/ELF ratio according to a plurality of predetermined step values $I_{S1}/I_{ELF1}$, $I_{S2}/I_{ELF2}$, $I_{S3}/I_{ELF3}$, $I_{Sn}/I_{ELFn}$, for corresponding time intervals $T_1$, $T_2$, $T_3$, $T_n$.

Preferably, the program means set the S and ELF fields according to an overall intensity between 1 and 30 mT and respectively a ratio S/ELF comprised between 0.1 and 10 and, in a particularly preferred embodiment, according to an overall intensity between 1 and 10 mT and respectively a ratio S/ELF comprised between 0.5 and 5.

The time intervals are preferably set between 1 and 40 minutes.

At least a portion of the working environment is defined by walls permeable to the S and ELF fields. At least a portion of the working environment is also advantageously adjacent to a first and a second coil respectively and the means for modulating supplying to the coils DC and AC current respectively.

BRIEF DESCRIPTION OF THE DRAWINGS

Several embodiments of the apparatus are shown in the attached drawings, given as an example and not limitative, wherein.

DESCRIPTION OF THE PREFERRED APPARATUS

Figure 1:
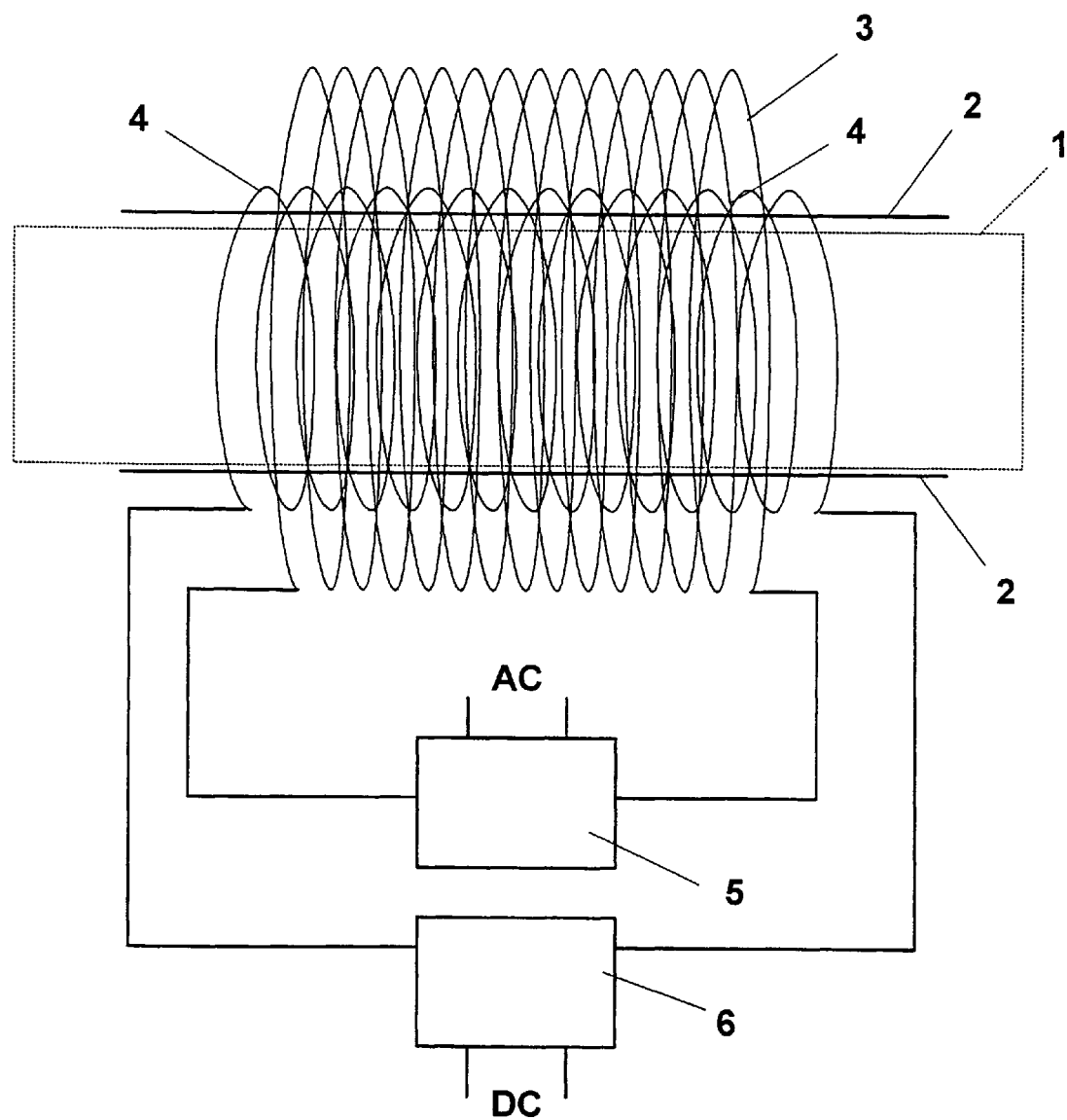
FIG. 1 shows a diagrammatical view of a first embodiment of an apparatus according to the invention.

In FIG. 1 the working environment is indicated as 1 and the wall as 2. The first and second coils are given the reference numbers 3 and 4 respectively. The modulating means are diagrammatically indicated by boxes 5 and 6 respectively, and are connected to AC and DC sources.

Figure 2:
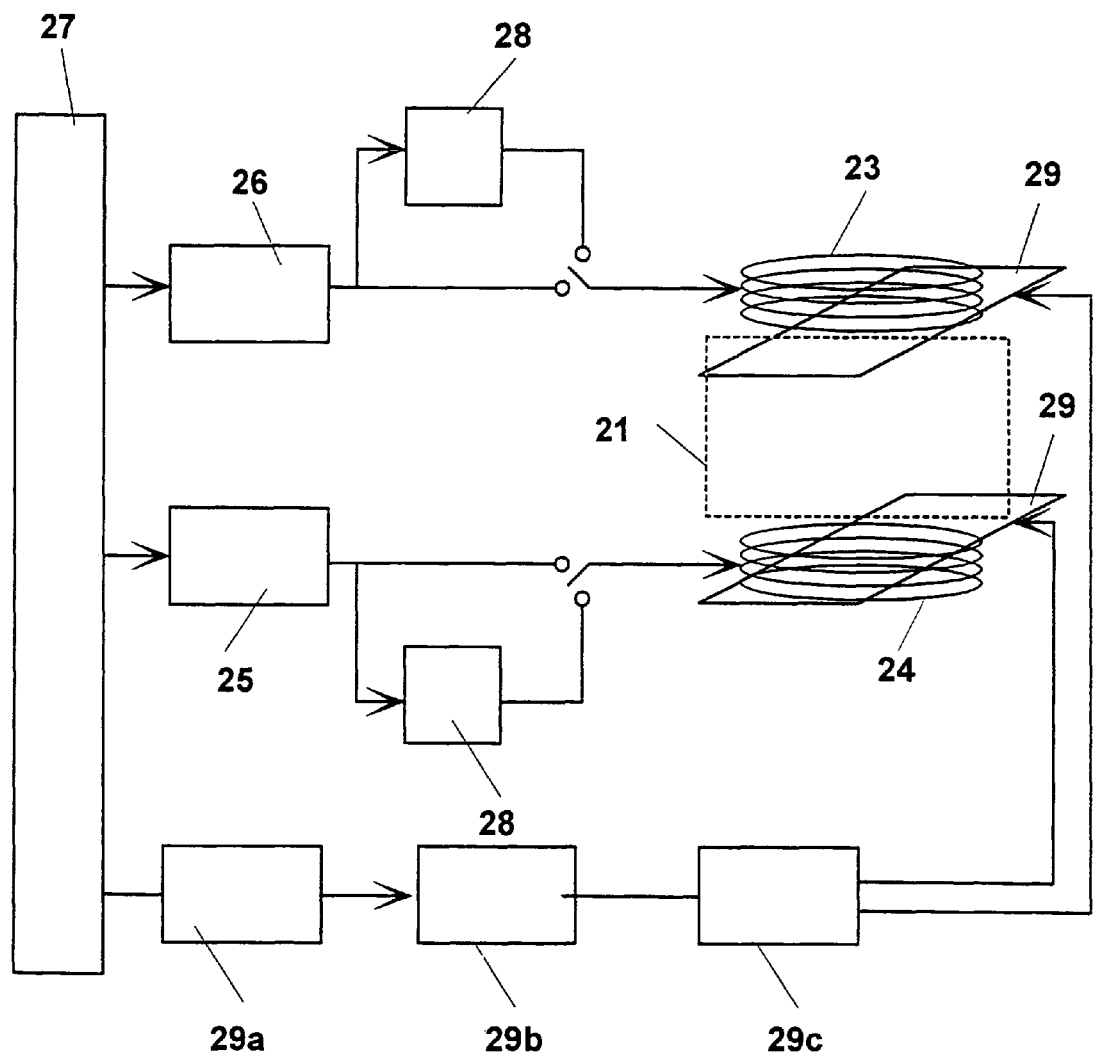
FIGS. 2 to 4 show block diagrams of a second third and fourth embodiment of an apparatus according to the invention, respectively.

In FIG. 2 a different embodiment of the apparatus, used for interfering with pathological cells survival both in vitro and in vivo, has two coils 23 and 24 located coaxial to each other at the opposite sides of the working environment 21. Variable transformers 25 and 26 are provided connected to a 50 Hz AC electric network 27. Switchable diode bridges 28 are provided to change the AC supply to the coils. A DC transformer 29a, a rectifier 29b as well as a timer 29c are provided supplying two plates 29 so that an up to 20 kV/m static (or low frequency variable up to 1000 Hz) electric field, and preferably about 6 kV/m, may be created in the working environment 21 within preferred intervals, according to the experimental conditions.

Figure 3:
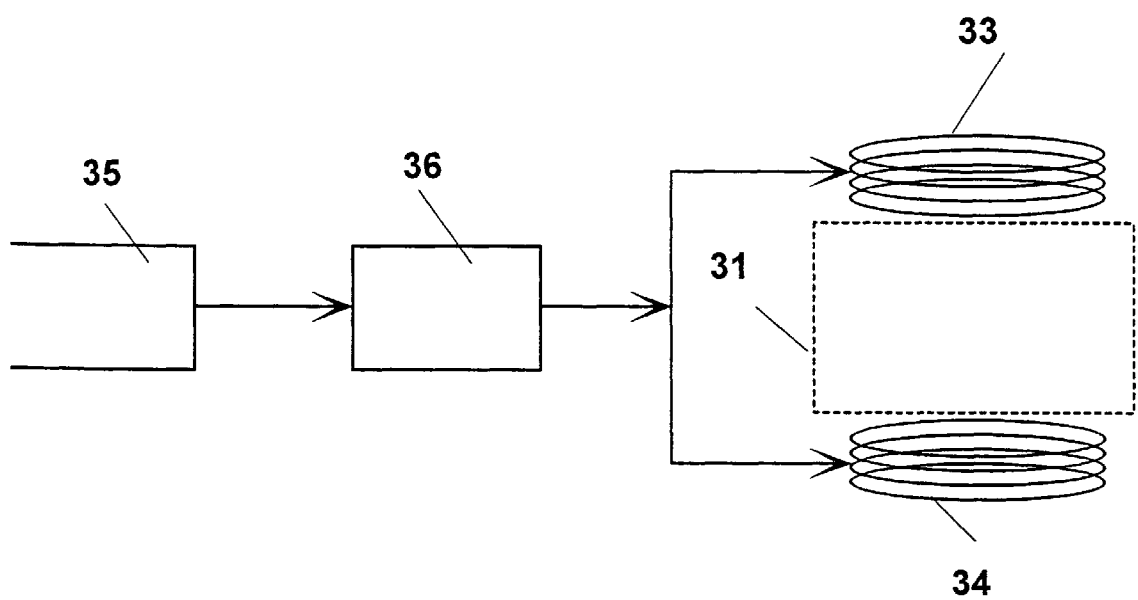

In FIG. 3 a further embodiment is shown of the apparatus used for interfering with pathological cells survival in vitro having a SELF modulator 35 (1-100 Hz) and two coils 33 and 34 located coaxial to each other at the opposite sides of the working environment 31. An amplifier 36 is used between the modulator 35 and the coils 33 and 34, which are supplied with the same current creating in the environment 31 either an S or an ELF magnetic field.

Figure 4:
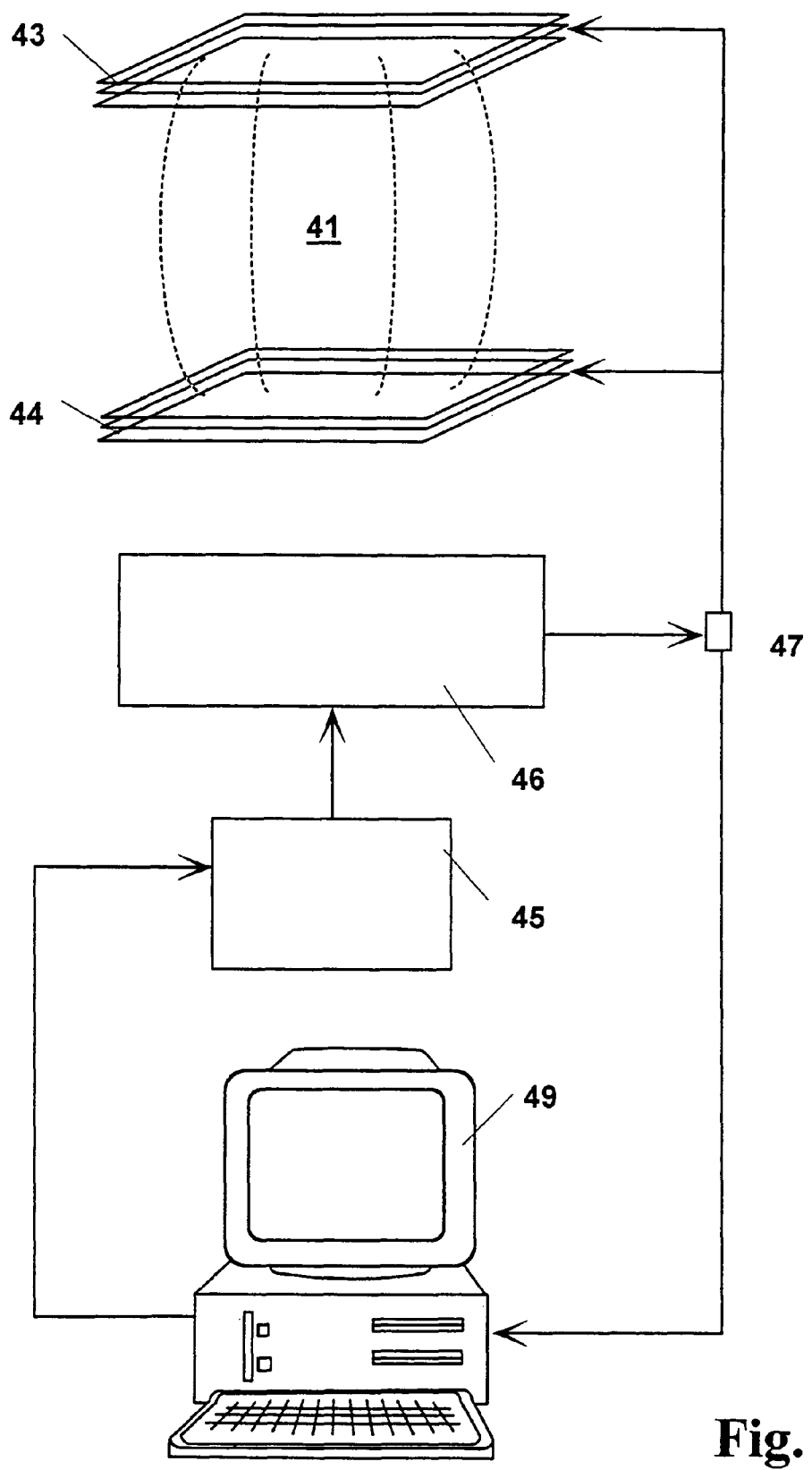

Another embodiment of the apparatus according to the invention (FIG. 4) used for interfering with pathological cells survival both in vitro and in vivo has two Helmoltz coils 43 and 44 located coaxial to each other at the opposite sides of the working environment 41. An amplifier 46 is used between the modulator 45 and the coils 43 and 44, through a shunt element 47, which is also connected to a personal computer 49.

Each apparatus can be used for producing SELF modulated non thermal fields for interfering with pathological cells survival.

Figure 5A:
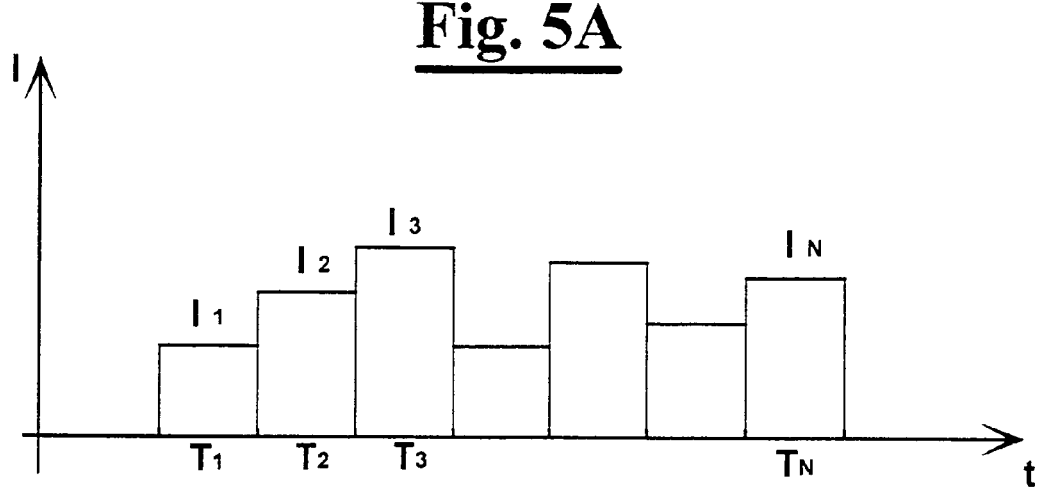
FIG. 5A shows a diagrammatic function of field intensity versus time, as programmable in the apparatus according to the invention.
Figure 5B:
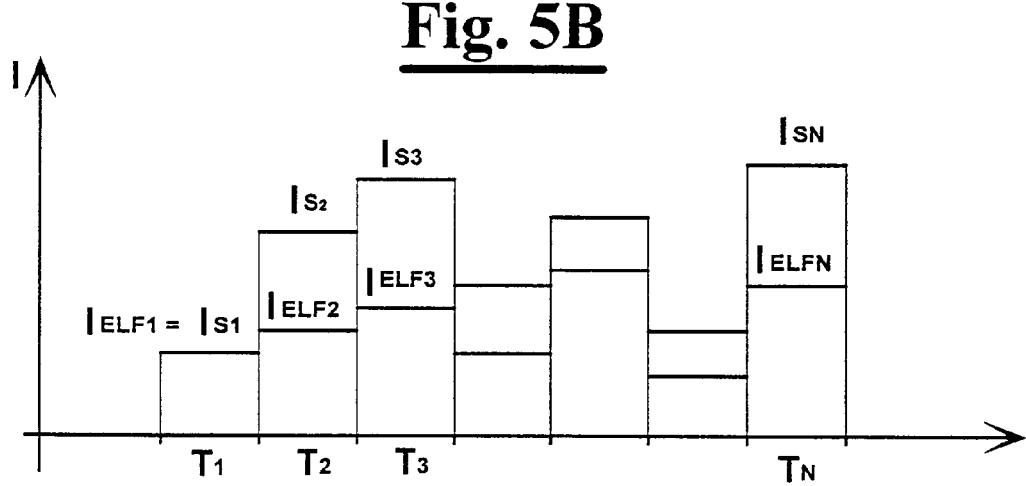
FIG. 5B shows a diagrammatic function of field intensity of S and ELF fields versus time varying also the ratio with respect to each other field.
Figure 5C:
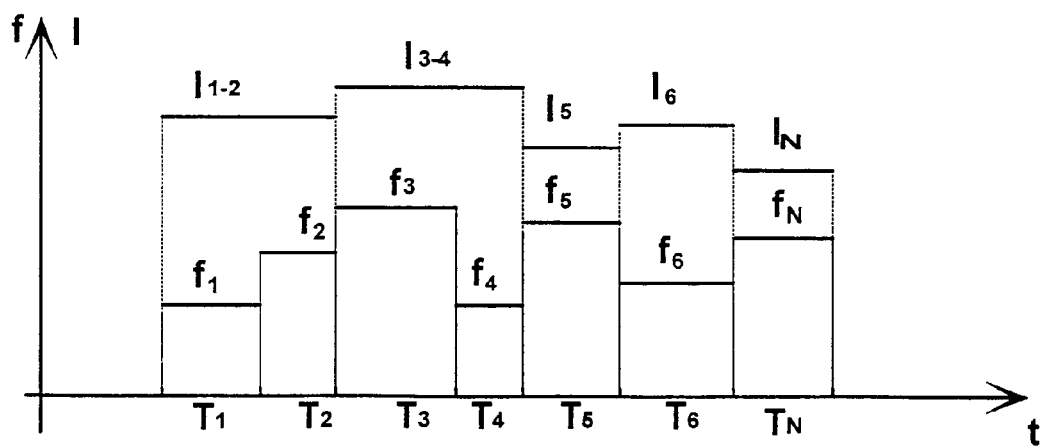
FIG. 5C shows a diagrammatic function of field intensity and frequency versus time.

With reference to FIGS. 5A to 5C, an example of the programming of the apparatus is given wherein the modulation of intensity, frequency and intensity ratio between S and ELF fields is carried out.

In FIG. 5A the way in which the intensity I may vary versus time. $I_1$, $I_2$, $I_3$, $I_n$ are the intensity or field strength (mT) of either the S field, or of the ELF field, or the overall intensity $I_S+I_{ELF}$.

In FIG. 5B, when both fields, S and ELF, are present, it is possible to modulate not only their intensity or intensity amplitude, but also their ratio $I_S/I_{ELF}$. For example, different ratios 1; 1.5; 2; etc. can be used for time intervals $T_1$, $T_2$; $T_3$; etc.

Also the frequency can be modulated as shown in FIG. 5C. The frequency may also be modulated in two or more following intervals $T_1$, $T_2$, wherein the same intensity $I_{1-2}$ is applied.

Starting from the basic examples of FIGS. 5A-5C a sequence of modulated S, ELF, S+ELF fields can be produced that can also be repeated cyclically.

The method according to the invention will now be described in more detail by way of specific examples.

EXAMPLE 1

In this experiment the capability of inducing apoptosis by SELF magnetic field as a function of field intensity and frequency was studied in vitro.

Human colon adenocarcinoma cell line (WiDr) grown in confluent monolayers in T25 flasks was used for the experiment. For each exposure condition 6 flasks containing each about 10 millions cells were used, 3 exposed and 3 shame-exposed (i.e. not exposed).

During the exposure the flasks were held between two coils connected with a circuit providing DC and AC currents up to 100 Hertz. The temperature was continuously monitored and maintained at 37±0.2° C.

The exposure duration was 20 minutes for each experiment and the SELF field was maintained constant. After 3 hours the cells were treated with May-Grunwald-Giemsa. Apoptosis was assessed by counting the number of apoptotic nuclei per 10 high power fields (HPF) by using an optic microscope.

The amount of induced apoptosis was evaluated by the ratio between the number of apoptotic cells found in the exposure group and the number of apoptotic cells found in the sham-exposed group, which is the group not exposed to the magnetic fields according to the invention.

Table 1 reports the results obtained in different exposure conditions.

TABLE 1

| exposure conditions | SELF field composition | frequency (Hz) | field intensity (Static + ELF rms) mT | apoptosis ratio |
|---|---|---|---|---|
| A | S (static) | – | (0.5 + 0) | 1 |
| B | S | – | (1 + 0) | 1 |
| C | S | – | (2 + 0) | 1.2 |
| D | S | – | (3 + 0) | 2 |
| E | S | – | (4 + 0) | 2.3 |
| F | S | – | (10 + 0) | 2.2 |
| G | S | – | (20 + 0) | 2.2 |
| H | S | – | (30 + 0) | 2.3 |
| I | ELF | 16 | (0 + 3) | 2.2 |
| L | ELF | 33 | (0 + 3) | 2.2 |
| M | ELF | 50 | (0 + 3) | 2.1 |
| N | ELF | 50 | (0 + 7) | 2.1 |
| O | ELF | 66 | (0 + 3) | 2.2 |
| P | ELF | 83 | (0 + 3) | 2.3 |
| Q | ELF | 100 | (0 + 3) | 2.1 |
| R | S + ELF | 50 | (4 + 3) | 2.1 |
| S | S + ELF | 50 | 50% of time (3 + 1) 50% of time (4.5 + 1.5) | 2.2 |

All the results were statistically highly significant (at the t Student test). From Table 1 we can see that the apoptosis effect appears at 2 mT and doubles starting from 3 mT.

Another important finding is that apoptosis doesn't depend upon SELF field frequency. In other words during the lifetime of the mechanism operating the biological effect (apoptosis) the ELF field is seen as essentially constant. This means that between the two hypothesised mechanism, free-radicals (occurring in a time scale of nano- to microsecond) and ion resonance-like mechanisms, the free radical one is playing the role [[39]Scaiano, 1994, [40]Engstrom, 1997].

EXAMPLE 2

In this experiment the selective effect of SELF magnetic fields was verified exposing three cell lines. Two lines were malignant, human colon adenocarcinoma cells (WiDr) and human breast cancer cells (MCF-7). The normal cell line was human lung fibroblast (MRC-5).

As in the example 1 each cell line was grown in confluent monolayers in T25 flasks. The experimental protocol was the same as in example 1. Six flasks (3 exposed and three shame-exposed) for each cell line were exposed for 20 minutes. Apoptosis was evaluated after 3 hours. The exposure conditions used were the R type of Table 1.

The results are reported in Table 2.

TABLE 2

| cell line | apoptosis ratio |
|---|---|
| WiDr | 2.1 |
| MCF-7 | 1.4 |
| MRC-5 | 1 |

As shown in Table 2 only cancer cells reported an apoptosis increment statistically highly significant, whereas the normal cell line didn't. The difference in percentage of apoptosis between the two cancer cell lines was expected due to the two different duplication times. In fact WiDr duplicates faster than MCF-7. The results were evaluated at t Student test.

EXAMPLE 3

In this example nude mice (nu/nu) bearing subcutaneous tumour masses were used to assess the influence of SELF magnetic fields on tumour growth inhibition.

Each mouse was inoculated subcutaneously with 10 million human colon adenocarcinoma cells (WiDr). Two experiments were successively carried out.

In the first experiment, 36 female mice were randomly assigned to 4 experimental groups, each formed by 6 exposed and 3 shame-exposed for a total of 24 animals exposed to 4 different SELF magnetic fields and 12 shame-exposed.

A Static Electric Field up to 6 kV/m was also applied to eventually take advantage of the different electrical behaviour between tumoral and normal tissues [[41]Thornton, 1984; [42]Barsamian, 1987]

In the second experiment 24 female mice were randomly assigned to 2 experimental groups, formed by 12 exposed to the SELF exposure condition which gave the best results among the four exposure conditions used in the previous experiment (exposure condition number 4), and 12 shame-exposed.

All the mice of both experiments were divided into experimental groups after the tumor masses for each animal were palpable.

The animals were exposed for 70 minutes, once a day, for 5 days a week, for 4 weeks. During the exposure each mouse was put in a single box made of Plexiglas held between two coils connected to a circuit providing DC and AC current up to 100 Hz respectively.

Nude mice were kept under specific pathogen free conditions and supplied with "ad libitum" diet. All the tests were conducted in accordance with the protocol issued by N.I.H. (US National Institute of Health) and N.C.I. (US National Cancer Institute).

The tumor masses were measured twice a week and their volume calculated in $mm^3$ according to the formula:

$$[(major\ diameter) \times (minor\ diameter\ squared)]/2.$$

After 4 weeks the animals were sacrificed and autopsied. Tumor masses were extracted, weighed and measured. Portions of tumors were used for different analysis, i.e.
- immunoistochemical: Ki-67 antigen for proliferative index, p-53 antigen for the expression of p-53 gene;
- hystopathological: hematossilina-eosin staining for the assessment of number of mitosis;
- ultrastructural: electron microscopy;
- nucleic acid hybridisation: Tunel method for apoptosis evaluation.

In addition, the following organs were extracted from each animal for histologic examination to assess the treatment toxicity: brain, heart, kidneys, liver, lungs, axillary and inguinal lymphonodes, mediastinal lymphonodes, ovaries, skin, spleen, bone marrow, subcutaneous tissue (site of tumoral cell line implantation) as well as blood tests.

The obtained results are reported in Table 3 for the first experiment and in Table 4 for the second.

with the hypothesised biophysical mechanism (i.e. free radical recombination) by which the SELF fields have an antitumor effect through formation of reactive oxygen species and the degradation of mitochondrial components.

TABLE 3

|  | exposure conditions | | | | |
|---|---|---|---|---|---|
|  | 1 | 2 | 3 | 4 | sham-exposed |
| exposure duration (min) | 70 | 70 | 70 | 70 | — |
| time averaged field intensity (Static + ELF rms) in mT | 3 | 3 | 4 | 6 | — |
| field variation in mT (min–max) | (4–6) | (1.5–4) | (2–5) | (2–5) | — |
| Static; [min–max] ELF | [2–2] | [1–1] | [1.5–3.5] | [1.5–3.5] | |
| constant field time duration (min–max) in minutes | (5–15) | (5–20) | (5–15) | (5–20) | — |
| time % with co-presence of Static and ELF fields | 0% | 50% | 50% | 100% | — |
| S/ELF ratio (min–max) | — | (0.5–5) | (0.5–5) | (0.5–5) | — |
| time % with Static field alone | 50% | 50% | 50% | 0% | — |
| number of mice | 6 | 6 | 6 | 6 | 12 |
| extracted tumor mass volume (mm$^3$) | 1323 ± 304 | 1450 ± 288 | 920 ± 540 | 650 ± 205 | 1492 ± 559 |
| extract tumor mass weight (g) | 1.54 ± 0.22 | 1.6 ± 0.39 | 0.98 ± 0.56 | 0.96 ± 0.25 | 1.6 ± 0.5 |
| number of apoptotic cells per 10 HPF | 98 ± 23 | 115 ± 20 | 129 ± 25 | 129 ± 26 | 40 ± 17 |
| p53 expression (antigen) per 10 HPF | 35.1 ± 0.11 | 43.8 ± 0.16 | 38.2 ± 0.06 | 28.7 ± 0.14 | 73.2 ± 0.14 |

TABLE 4

|  | exposure conditions | |
|---|---|---|
|  | 4 (see tab. 3) | sham exposed |
| number of mice | 12 | 12 |
| extracted tumor mass volume | 1139 ± 509 cm$^3$ | 1914 ± 793 cm$^3$ |
| extracted tumor mass weight | 1.4 ± 0.7 g | 2.1 ± 0.6 g |
| apoptosis (assessed in 50% of mice only) | 72.5 ± 9.3 | 37.0 ± 7.4 |
| p53 | 35.6 ± 6.7 | 78.1 ± 16.7 |
| proliferative index | 0.34 ± 0.08 | 0.45 ± 0.07 |
| mitosis | 24.1 ± 10.9 | 47.7 ± 10.1 |

The data reported in Tables 3 and 4 show that SELF fields have an inhibitory tumor growth effect in vivo. This effect, found in both experiments, was statistically highly significant (in the first experiment, mostly for the exposure condition 4) at the Dunnet and t Student tests respectively.

At the histologic examination of 12 organs for each animal for all groups no differences were found between exposed and shame-exposed mice. No differences were also found in the blood tests. These findings prove the absence of toxicity related to the SELF fields treatment.

The ultrastructural analysis by electron microscope showed in the tumor cells of exposed animals many cellular alterations: presence of apoptotic bodies and condensed chromatin near the nuclear membrane characteristic of apoptotic events.

In addition a consistent result is represented by morphological modifications, increase of number and dimensions of mitochondria as well as number of nucleoli, presence of many vacuoles inside the cytoplasm. Non neoplastic cells (i.e. epithelial and stromal cells) showed no differences between exposed and shame-exposed animals in agreement with the absence of toxicity found in 12 normal organs examined in each animal.

The increment in apoptosis as well as the decrement in p53 gene expression found in exposed mice tumors (see tables 3 and 4) are statistically highly significant (t Student test) Results reported in Table 3 and 4 are in agreement with those obtained in vitro and shown in Tables 1 and 2.

The effect induced by the SELF magnetic fields on p53 expression enforces the apoptosis results and is in agreement

EXAMPLE 4

In this experiment nude mice (nu/nu) previously subcutaneous inoculated with 10 million human colon adenocarcinoma cells (WiDr) were exposed to study the animal survival.

After the cell inoculation 2 groups of mice were randomly formed respectively of 16 animals exposed and 17 shame-exposed. The mice of the former group were exposed 70 minutes once a day, for 5 days a week, for their entire life beginning after 24 hours after the tumor inoculation.

The exposure conditions were the same of the experiment the results which are reported in Table 4.

As in the previous example, the mice were maintained under specific pathogen free condition supplied with "ad libitum" diet. All the tests were conducted in accordance with protocol issued by N.I.H. and N.C.I.

The antitumor effectiveness of the treatment was evaluated by using the N.C.I. formula: ratio between exposed and shame-exposed animals of the average animal life span. This average was evaluated summing for each experimental group the time of survival divided by the number of animals. The effectiveness is obtained when the N.C.I. formula gives as result an index equal or greater than 1.25.

Table 5 reports for each experimental group, the number of living animals at different times (days) from the beginning of experiment.

TABLE 5

| living mice exposed/ | 16/16 | 16/15 | 15/14 | 14/14 | 13/14 | 12/14 |
|---|---|---|---|---|---|---|
| shame-exp. (days) | (48) | (73) | (76) | (84) | (87) | (88) |
| living mice exposed/ | 12/13 | 12/12 | 10/12 | 10/10 | 10/9 | 9/8 |
| shame-exp. (days) | (97) | (107) | (109) | (114) | (115) | (125) |
| living mice exposed/ | 9/7 | 8/6 | 8/5 | 8/4 | 7/4 | 7/3 |
| shame-exp. (days) | (149) | (153) | (155) | (157) | (163) | (173) |
| living mice exposed/ | 6/3 | 6/2 | 6/0 | 5/0 | 4/0 | 3/0 |
| shame-exp. (days) | (183) | (192) | (194) | (195) | (203) | (257) |
| living mice exposed/ | 2/0 | 1/0 | | 0*/0 | | |
| shame-exp. (days) | (276) | (323) | | *sacrificed (326) | | |

The N.C.I. formula applied to the results reported in Table 5 gives an index equal to 1.31, which is greater than 1.25. After 194 days 6 exposed mice were alive whereas all shame exposed mice were dead.

The foregoing description of specific embodiments will so fully reveal the invention according to the conceptual point of view, so that others, by applying current knowledge, will be able to modify and/or adapt for various applications such embodiments without further research and without departing from the invention, and it is therefore to be understood that such adaptations and modifications will have to be considered as equivalent to the specific embodiments. The means and the materials to realise the different functions described herein could have a different nature without, for this reason, departing from the field of the invention. It is to be understood that the phraseology or terminology employed herein is for the purpose of description and not of limitation.

REFERENCES

1. Blank M (1993): "Electricity and Magnetism in Biology and Medicine". The First World Congress for Electricity and Magnetism in Biology and Medicine, Orlando, Fla.
2. Liboff A R, Williams T Jr, Strong D M and Wistar R. Jr. (1984): "Time-Varying Magnetic Fields: Effect on DNA Synthesis". Science, Vol. 223, pp 818-820.
3. Tofani S, Ferrara A, Anglesio L, Gilli G (1995): "Evidence for genotoxic effects of resonant ELF magnetic fields". Bioelectrochemistry and Bioenergetics 36, pp 9-13.
4. Goodman R, Shirley-Henderson A (1991): "Transcription and Translation in Cells exposed to Extremely Low Frequency Electromagnetic Fields" Bioelectrochem. Bioenerg. 25, pp. 335-355.
5. Phillips j l, Haggren w, Thomas W J, Ishida-Jones T and Adey W R (1992): "Magnetic field-induced changes in specific gene transcription". Biochimica et Biophysica Acta 1132, pp 140-144.
6. Liboff A R (1985): Cyclotron resonance in membrane transport. In Chiabrera A, Nicolini C., Schwan H P (eds): "Interactions Between Electromagnetic Fields and Cells". New York: Plenum Press, pp 281-296.
7. Chiabrera A., Grattarola M., Viviani R. (1984): "Interaction between electromagnetic fields and cells: Microelectrophoretic effect on ligands and surface receptors". Bioelectromagnetics 5, pp 173-191.
8. Lednev V V (1991): "Possible mechanism for the influence of weak magnetic fields on biological systems". Bioelectromagnetics 12, pp 71-75.
9. Blanchard J P, Blackman C F (1994): "Clarification and application of an ion parametric resonance model for magnetic field interactions with biological systems. Bioelectromagnetics 15, pp 217-238.
10. Preston G A, Barrett J C, Biermann J A and Murphy Elizabeth (1997): "Effects of Alterations in Calcium Homeostasis on Apoptosis during Neoplastic Progression", Cancer Research 57, pp. 537-542.
11. Trump B F, Berezesky I K, Chang S H and Phelps P C (1997): "The Pathways of Cell Death: Oncosis, Apoptosis, and Necrosis". Toxicologic Pathology Vol. 25, n. 1, pp. 82-87.
12. Grundler W, Kaiser F, Keilmann F, Walleczek J (1992): "Mechanisms of electromagnetic interaction with cellular systems". Naturwissenschaften 79, pp. 551-559.
13. Polk C (1992): "Dosimetry of extremely-low-frequency magnetic fields". Bioelectromagnetics Suppl 1, pp. 209-235
14. Walleczek J, Budinger T F (1992): "Pulsed magnetic field effects on calcium signalling in lymphocytes: Dependence on cell status and field intensity". FEBS Lett 314, pp 351-355.
15. Adey W R (1993): Electromagnetics in biology and medicine. In Matsumoto H (ed): "Modern Radio Science", New York: Oxford University Press, pp 227-245.
16. Steiner U E and Ulrich T (1989): "Magnetic Field Effects in Chemical Kinetics and Related Phenomena". Chem. Rev. 89, pp. 51-147.
17. Lander H M (1997): "An essential role for free radicals and derived species in signal transduction". The FASEB Journal 11, pp 118-124.
18. Polyak K, Xia Y, Zweier J L, Kinzier K W and Volgestein B (1997): "A model for p53-induced apoptosis". Nature Vol. 389, pp. 300-305.
19. (18). Walch, N. S., Calaoagan, J., Murphy, B. J., Knapp, A. M., Sutherland, R. M., Laderoute, K. R. "The redox-sensitive human antioxidant responsive element induces gene expression under low oxygen conditions". Carcinogenesis, 19 (8): 1333-7, 1988.
20. Amirkhosravi, A., Meyer, T., Warnes, G., Amaya, M., Malik, Z., Biggerstaf, J. P., Siddiqui, F. A., Sherman, P., Francis, J. L. Pentoxifylline inhibits hypoxia-induced upregulation of tumor cell tissue factor and vascular endothelial growth factor. Thromb Haemost, 80 (4): 598-602, 1998.
21. Cadossi R, Bersani F, Cossarizza A, Zucchini P, Emilia G, Torelli G and Claudio Franceschi (1992): "Lymphocytes and low-frequency electromagnetic fields". The FASEB Journal Vol. 6, pp. 2667-2674.
22. Walleczeck J (1996): "Electromagnetic Field Effects on Cellular Signal Transduction and Free Radical Mechanisms". Abstract Book XXVth General Assembly of the International Union of Radio Science-Lille-France, p. 547.
23. Binggeli R, Weinstein R C. Membrane potentials and sodium channels: hypotheses for growth regulation and cancer formation based on changes in sodium channels and gap junctions. Theor Biol 1986: 123:377-401.
24. Marino A A, Iliev I G, Schwalke M A, Gonzales E, Marler K C, Flanagan C A. Association between cell membrane potential and breast cancer Tumour Biol. 1994: 15:82-89.
25. Davies R J, Weidema W F, Sandle G I, Palmer L I, Deschener E E, DeCosse J J. Sodium transport in a mouse model of colonic cancer. Cancer Res. 1987: 47:4646-50.
26. Goller D A, Weidema W F, Davies R J. Transmural electrical potential as an early marker in colon cancer. Arch. Surg. 1986: 121:345-50.
27. Capko D, Zhuravkov A, Davies R J. Transepithelial depolarisation in breast cancer. Breast Cancer Res. 1996: Treat. 41:230.
28. Cuzick J, Holland R., Barth V, Davies R, Faupel M, Fentiman I, Frischbier H J, LaMarque J L, Merson M, Sacchini V, Vanel D, Veronesi U. Electropotential measurements, as a new diagnostic modality for breast cancer. The Lancet 1998: 352:359-363.
29. Szatrowski T P, Nathan C F. Production of of large amounts of hydrogen peroxide by human tumor cells. Cancer Res. 1991: 51 (3):794-798.
30. Shulyakovskaya T, Sumegi L, Gal D. In vivo experimental studies on the role of free radicals in photodynamic therapy. I. measurement of the steady state concentration of free radicals in tumor tissues of mice. Biochem. Biophys. Res. Commun. 1993: 195 (2):581-587.
31. Iwagaki H, Hamazaki K, Matsubara N, Hiramatsu M, Orita K, Mori A. Lipid peroxidation in hepatocellular carcinoma. Acta Med. Okayama 1995: 49 (6):313-315.
32. Levin V A (1998): "Signal Transduction Directed Therapy: Fact or Fantasy?" Abstract Book (EL 5) of the Eight International Congress on Anti-Cancer Treatment, Feb. $3^{rd}$-$6^{th}$ 1998, Paris, France.
33. Thompson C. B. (1995): "Apoptosis in the pathogenesis and treatment of diseases" Science Vol. 267, p. 1456-1462

34 Costa J L and Hofmann G A (1987): "Malignancy treatment" U.S. Pat. No. 4,665,898.
35 Narita K, Hanakawa K, Kasahara T, Hisamitsu T, Asano K (1997): "Induction of apoptotic cell death in human leukemic cell line, HL-60, by extremely low frequency electric magnetic fields: analysis of the possible mechanisms in vitro". In vivo 111(4), pp. 329-335.
36 Raylman R R, Clavo A C, Wahl R L (1996): "Exposure to Strong Static Magnetic Field Slow the Growth of Human Cancer Cells In Vitro". Bioelectromagnetics 17, pp. 358-363.
37 Haberkorn R, Michel-Beyerle M E. On the mechanism of magnetic field effects in bacterial photosynthesis. Biophysical Journal 1979: 26:489-498.
38 Lersch W, Michel-Beyerle M E. Magnetic field effects on the recombination of radical ions in reaction centers of photosynthetic bacteria. Chemical Physics 1983: 78:115-126.
39 Scaiano J C, Mohtat N, Cozens F L, McLean J and Thansandote (1994): "Application of the Radical Pair Mechanism to Free Radicals I Organized Systems: Can the Effects of 60 Hz Be Predicted From Studies Under Static Fields?" Bioelectromagnetics 15, pp. 549-554.
40 Engstrom S (1997): "What is the Time of Magnetic Field Interaction in Biological Systems?". Bioelectromagnetics 18, pp. 244-249.
41 B. S. Thornton (1984): "Inversion of raman spectra of living cells indicates dielectric structure related to energy control", in Physics Letters, Vol. 106A, pp. 198-202.
42 S. T. Barsamian (1987): "Dielectric origin of living cells", in Biophysical Aspects of Cancer, Charles University Prague, pp. 152-159

What I claim is:

1. A method for selectively interfering with pathological cells survival processes in vitro and in vivo comprising:
arranging a tissue containing said cells in a working environment,
generating static magnetic (S) fields crossing said working environment,
generating electromagnetic extremely low frequency (ELF) fields over said working environment in addition to said S fields;
modulating said S fields, setting the intensity of said S fields between 1 and 100 mT according to a predetermined function of intensity versus time;
modulating said ELF fields according to a predetermined function of amplitude of intensity between 1 and 100 mT and frequency between 1 and 1000 Hz versus time;
wherein said step of modulating said S fields provides setting intensity values $I_{S1}, I_{S2}, \ldots, I_{SN}$ of said S fields for respective time intervals $T_1, T_2, \ldots, T_n$,
wherein said step of modulating said ELF fields comprises setting intensity values $I_{ELF1}, T_{ELF2}, \ldots, I_{ELFn}$ of said ELF fields for said respective time intervals $T_1, T_2, \ldots, T_n$.
and wherein said step of modulating said S and ELF fields comprises setting an S/ELF intensity ratio according to a plurality of predetermined values $I_{S1}/I_{ELF1}, I_{S2}/I_{ELF2}, \ldots, I_{Sn}/I_{ELFn}$, for said respective time intervals $T_1, T_2, \ldots, T_n$.

2. The method according to any of claim 1 wherein said step of modulating said ELF fields comprises setting frequency values $f_1, f_2, \ldots, f_n$, of said ELF fields for said respective time intervals $T_1, T_2, \ldots, T_n$, to frequency values of between 10 and 100 Hz.

3. The method according to claim 1, wherein said step of modulating said S and ELF fields comprises setting said S and ELF fields according to an overall intensity of between 1 and 30 mT and respectively an intensity ratio S/ELF of between 0.1 and 10.

4. The method according to claim 1, wherein said step of modulating said S and ELF fields comprises setting said S and ELF fields according to an overall intensity between 1 and 10 mT and respectively a ratio S/ELF comprised between 0.5 and 5.

5. The method according to claim 1 wherein said time intervals $T_1, T_2, \ldots, T_n$ are set between 1 and 40 minutes.

6. The method according to claim 1 wherein at least a portion of said working environment is defined by walls permeable to said fields.

7. The method according to claim 1, wherein a static electric field is generated over said working environment in addition to said S and ELF fields, wherein said electric field has an intensity lower than 20 kV/m.

8. The method according to claim 1 wherein said cells are selected from the group comprised of cells affected by cancer, cells affected by viral infections, cells affected by autoimmune diseases, cells affected by neurodegenerative disorders, cells affected by AIDS, and cells having mutant p53 gene.

* * * * *